United States Patent
Persson

(10) Patent No.: US 9,415,180 B2
(45) Date of Patent: Aug. 16, 2016

(54) BREATHING PROTECTOR

(75) Inventor: Jan-Ove Persson, Höör (SE)

(73) Assignee: Atos Medical AB (SE)

( * ) Notice: Subject to any disclaimer, the term of this patent is extended or adjusted under 35 U.S.C. 154(b) by 804 days.

(21) Appl. No.: 13/583,542

(22) PCT Filed: Mar. 8, 2011

(86) PCT No.: PCT/EP2011/053455
§ 371 (c)(1),
(2), (4) Date: Jan. 17, 2013

(87) PCT Pub. No.: WO2011/110549
PCT Pub. Date: Sep. 15, 2011

(65) Prior Publication Data
US 2013/0239958 A1   Sep. 19, 2013

Related U.S. Application Data

(60) Provisional application No. 61/311,446, filed on Mar. 8, 2010.

(51) Int. Cl.
*A61M 16/04* (2006.01)
*A61M 16/10* (2006.01)

(52) U.S. Cl.
CPC ......... *A61M 16/047* (2013.01); *A61M 16/1045* (2013.01); *A61M 16/1055* (2013.01); *A61M 16/0465* (2013.01); *A61M 16/0468* (2013.01); *Y10T 29/49826* (2015.01); *Y10T 29/53* (2015.01)

(58) Field of Classification Search
CPC .......... A61M 16/0465; A61M 16/047; A61M 16/1045; A61M 16/105; A61M 16/1055
USPC ............. 128/201.13, 205.27, 205.29; 29/428, 29/700, 896.62, 902
See application file for complete search history.

(56) References Cited

U.S. PATENT DOCUMENTS 4,273,119 A * 6/1981 Marchello ................ A61D 7/04
119/832
4,538,607 A * 9/1985 Saul .................. A61M 16/0468
128/207.16

(Continued)

FOREIGN PATENT DOCUMENTS

CN           102781504 A     11/2012
DE      102005007234 B3      7/2006

(Continued)

OTHER PUBLICATIONS

English translation of Chinese office action for CN-20132179341.0, dated Jul. 31, 2013.

(Continued)

*Primary Examiner* — Tan-Uyen (Jackie) T Ho
*Assistant Examiner* — Joseph D Boecker
(74) *Attorney, Agent, or Firm* — Fishman Stewart PLLC

(57) ABSTRACT

A breathing protector may include an inlet and an outlet, wherein an air flow may be configured to pass from the inlet to the outlet into a trachea. A filter housing may include an inner housing part, an outer housing part, and a filter body. The inner housing party may include the outlet, a tracheal tube fitting and a support structure extending longitudinally and distally from the tracheal tube fitting. A base plate may be arranged in a proximal zone of the tracheal tube fitting and extend radially outwards from the tracheal tube fitting. The outer housing part may include the inlet and form a cage enclosing the support structure. The filter body may be arranged between the support structure and the outer housing part.

23 Claims, 4 Drawing Sheets

(56) References Cited

U.S. PATENT DOCUMENTS

| | | | |
|---|---|---|---|
| 5,020,534 A * | 6/1991 | Pell | A61M 16/0488 128/207.14 |
| 5,022,394 A * | 6/1991 | Chmielinski | A61M 16/1045 128/206.17 |
| 5,042,468 A * | 8/1991 | Lambert | A61M 16/1045 128/200.24 |
| 5,195,527 A * | 3/1993 | Hicks | A61M 16/105 128/204.17 |
| 5,487,382 A | 1/1996 | Bezicot | |
| 5,606,966 A * | 3/1997 | Smith | A61M 16/0465 128/200.26 |
| 6,363,930 B1 * | 4/2002 | Clawson | A61M 16/1045 128/201.13 |
| 6,422,235 B1 | 7/2002 | Persson | |
| 6,921,417 B2 * | 7/2005 | Persson | A61F 2/20 623/9 |
| 7,059,327 B2 * | 6/2006 | Worthington | A61F 2/20 128/200.26 |
| 7,993,071 B2 * | 8/2011 | Clawson | A61M 16/1045 277/641 |
| 2002/0156527 A1 | 10/2002 | Persson | |
| 2010/0288284 A1 * | 11/2010 | Persson | A61M 16/0468 128/207.14 |
| 2011/0220108 A1 * | 9/2011 | Persson | A61M 16/0468 128/205.29 |
| 2012/0090621 A1 * | 4/2012 | van der Houwen | A61M 16/0468 128/207.16 |
| 2013/0192602 A1 * | 8/2013 | Leibitzki | A61M 16/0468 128/205.27 |
| 2013/0192603 A1 * | 8/2013 | Leibitzki | A61M 16/0468 128/205.29 |
| 2013/0269702 A1 | 10/2013 | Persson | |
| 2014/0150779 A1 * | 6/2014 | Persson | A61M 16/1055 128/201.13 |
| 2015/0083119 A1 * | 3/2015 | Persson | A61M 16/0468 128/201.13 |

FOREIGN PATENT DOCUMENTS

| | | | |
|---|---|---|---|
| GB | 2303553 A | 2/1997 | |
| GB | 2322568 A | 9/1998 | |
| JP | H10-235126 A | 9/1998 | |
| JP | 2002-516144 A | 6/2002 | |
| WO | WO 2008132222 A2 * | 11/2008 | A61M 16/0468 |

OTHER PUBLICATIONS

English abstract for DE-102005007234.

* cited by examiner

BREATHING PROTECTOR

CROSS-REFERENCES TO RELATED APPLICATIONS

This application is a National Stage application which claims the benefit of International Application No. PCT/EP2011/053455 filed Mar. 8, 2011, which claims priority based on U.S. Provisional Patent Application 61/311,446, filed on Mar. 8, 2010, both of which are hereby incorporated by reference in their entirety.

FIELD OF THE INVENTION

This invention pertains in general to the field of a breathing protector for use in a stoma of a laryngectomized or tracheotomised person, said breathing protector having at least one inlet and at least one outlet, such that an air flow in use will pass from the surroundings of said person through said inlet to said outlet, into trachea of said person, said breathing protector comprising a heat-moisture exchanger and a bacteriological filter, such that said air flow will pass through said heat-moisture exchanger and said bacteriological filter when said air flow in use passes through said inlet to said outlet.

BACKGROUND OF THE INVENTION

A tracheostomy is a surgical procedure in which an opening is formed through the anterior surface of the neck into the trachea. The opening is referred to as a tracheostoma. A tracheostomy tube can be provided to extend between the tracheostoma and the trachea. A tracheostomy is performed for example when there is a malfunction, such as a result from injury or disorder, in respect of the nervous system or the respiratory passages, which malfunction results in an incapacity to obtain enough air. An inferior lung capacity or need of respiratory treatment may also result in a tracheostomy.

A laryngectomy is a surgical procedure, used for example to treat a carcinoma, which involves removal of the larynx or voice box and creation of a tracheostoma. A consequence of the procedure is that the trachea is no longer connected to the pharynx but is diverted to the tracheostoma. After this procedure, normal nasal function is not possible. In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and microorganisms, from the inhaled air, and the action of cilia transports mucous and any particles away from the lungs.

When a patient has received a laryngectomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the patient to speak. It is desirable that the flow of the exhaled air be controlled by means of a tracheostoma valve. In these situations, the valve can be arranged to remain open during breathing but, with a small additional increase in exhaled air flow, can be closed to divert the airflow.

In this respect filter devices and breathing protectors have been developed to enable moisturizing of inhaled air and removal of small particles and bacteriological substances in said inhaled air, to ensure minimized spreading of virus and bacteria. This has especially being an issue when the same respirator is used for multiple patients. This is to resemble the functions of a nose. However, there are several complications related to the design of such devices. Firstly, the user of such devices is in need of good moisturizing and filtering effect while keeping the size, such as the dead space area or volume, of the device as small as possible. Otherwise, the device will be unsuitable for children. Secondly, the moisturizing effect and filter effect is in need of large surface area, while not creating a too large resistance over the device. These criterions are contradictive, which the observant reader already has acknowledged. Also, a laryngectomy has to hold his finger or thumb over these devices when wishing to speak, to thereby obstruct the air flow through the device and the stoma through the tracheal wall, which will burden the filter with undue contamination, due to transfer of impurities from the finger of the user to the filter.

U.S. Pat. No. 5,848,590 discloses a filter assembly for filtering air that is to be breathed through a tracheostoma, comprising a housing and a filter component. The filter component is however movable within the housing, forcing the filter component and heat-moisture exchanger to be glued into one piece, forcing the additional manufacturing steps, making the manufacturing procedure complicated, time consuming, and thus costly. U.S. Pat. No. 5,666,950 discloses a similar filter component and device arrangement. Also, the filtering effect of these planar filters is very low.

WO 2008/132222 discloses a breathing protector for use in a stoma of a laryngectomized person. The breathing protector is provided with a heat-moisture exchanger, a bacteriological filter, and a closing mechanism. However, the proximal side is prone to contact the skin of the patient, and thus there is a risk for clogging and contaminating the filter. Also, because of the closing mechanism, the breathing protector of this kind has a large dead space, making the device large and increasing dead space, and hence not so usable for children. Also, a too large dead space results in a decrease in fresh air reaching the lungs of the patient. Furthermore, the arrangement of the different parts into the breathing protector necessitates gluing/welding, or other attachment means, making the manufacturing procedure complicated, time consuming, and thus costly.

Hence, it would be beneficial with a new breathing protector, allowing for a small, and space effective device, said device comprising a heat-moisture exchanging and bacterial/viral filtrating function with guarded filter surfaces, while simultaneously allowing for the possibility to omit specially designed filter bodies with unnecessary adhesion substances/elements there between. It would also be beneficial with arrangements and parts allowing for an easy assembling of such new breathing protectors.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a breathing protector for a tracheostoma, comprising an inlet and an outlet, such that an air flow in use will pass from the surroundings of the user through said inlet to said outlet, into trachea of said user, said breathing protector comprising a filter housing, said filter housing comprising an inner housing part, an outer housing part, and a filter body; wherein the inner housing part, comprising the outlet, a tracheal tube fitting and a support structure extending longitudinally and distally from the tracheal tube fitting, wherein a base plate is arranged in a proximal zone of the tracheal tube fitting, said base plate extending radially outwards from the tracheal tube fitting; wherein the outer housing part, comprising the inlet, forming a cage enclosing the support structure; and wherein the filter body is arranged between the support structure and the outer housing part; a breathing protector assembling tool comprising a fixture part for holding an outer housing part in an assembly position, said fixture part comprising a cavity for receiving the outer housing part; channels extending transversally to the longitudinal extension of the cavity and intersecting said cavity, said channels being configured for receiving filter adjustment sticks there through; and a method for assembling a breathing protector according to above, comprising the steps: arranging an outer housing part in a cavity of a breathing protector assembling tool according to above; arranging at least a filter body at the mouth of a cavity of a breathing protector assembling tool; and pressing a inner housing part into the cavity, such that the filter body is arranged beneath said inner housing part, until the inner housing part is brought into cooperation with said outer housing part, according to the appended patent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

The following description focuses on an embodiment of the present invention applicable to a breathing protector, and particularly to a breathing protector for application over the tracheostoma of a tracheostomized person.

Figure 1:
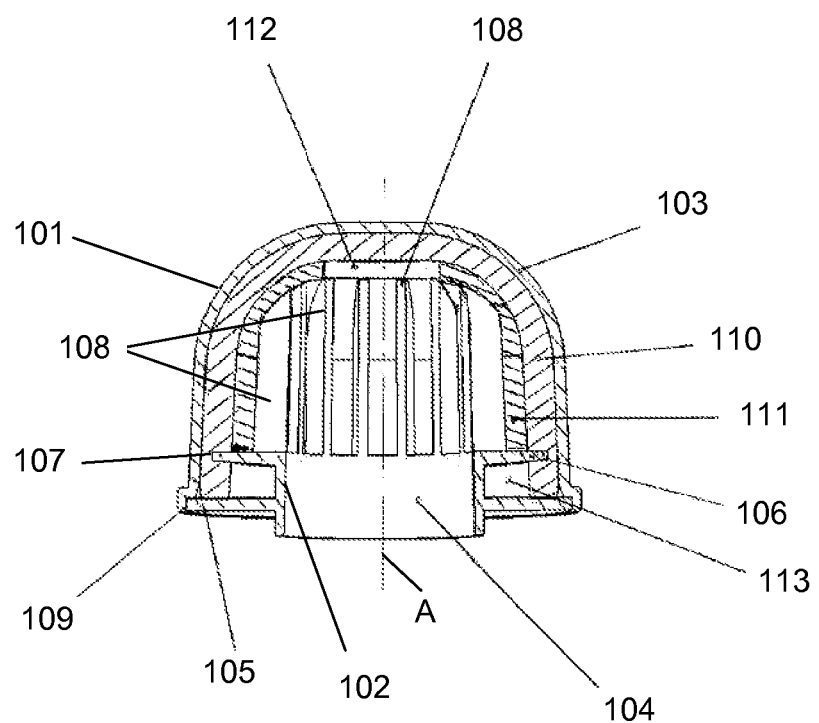
FIG. 1 is a cross sectional view of a breathing protector according to one embodiment of the present invention.

In an embodiment of the invention, according to FIG. 1, a breathing protector for a tracheostoma is provided. The breathing protector comprises a filter housing 101. The filter housing 101 comprises an inner housing part 102 and an outer housing part 103. The inner housing part 102 and the outer housing part 103 may be injection molded in a suitable polymeric material, such as poly propylene.

The inner housing part 102 comprises a tracheal tube fitting, in form of a cylindrical body 104. The cylindrical body 104 extends longitudinally in the proximodistal direction, with a central axis A. The cylindrical body 104 may have slightly decreasing cross sectional area in the transversal plane when moving distally along the cylindrical body 104. Thus, the cylindrical body may have a conical shape or cut-conical shape. The tracheal tube fitting may preferably have an ISO-15 cone, to be connectable to standard tracheal tubes.

In the proximal zone of the tracheal tube fitting, such as the cylindrical body 104, a base plate 105 extends radially outwards from the tracheal tube fitting. The base plate 105 then extends substantially in the transversal plane with respect to the cylindrical body 104. The peripheral shape of the base plate 105 in the transversal plane may have different shapes, in correspondence with the shape of the outer housing part 103. However, circular and elliptical shapes are preferred, due to facilitated manufacturing and assembling of the breathing protector. Also, the design is more pleasing. Other possible peripheral shapes in the transversal plane are triangular, rectangular, square, or other multiangular shapes. The outer edge of the base plate 105 may be slanting slightly laterally downwards, such that cooperation with the outer housing part 103 may be facilitated.

On the tracheal tube fitting, such as the cylindrical body 104, a pinch plate 106 is arranged distally of the base plate 105. The pinch plate 106 extends radially outwards from the tracheal tube fitting. The pinch plate 106 then extends substantially in the transversal plane with respect to the cylindrical body 104. The peripheral shape of the pinch plate 106 in the transversal plane may have different shapes, in correspondence with the shape of the outer housing part 103 and the base plate 105. The base plate 105 extends laterally beyond the pinch plate 106, such that the outer housing part 103 may extend distally from the base plate, after being connected to the same, laterally of the pinch plate 106. The pinch plate 106 may have an outer flange 107, for improved pinching function in accordance with below.

Support structure 108 extends longitudinally and distally from the tracheal tube fitting, such as the cylindrical body 104, and/or the pinch plate 106. The support structure 108 may be support fingers, support bars, support ribs, with slots there between. The support structure 108 may also be a perforated grid or rail. The support structure shall support heat-moisture exchanger and filter body, in an evenly distributed manner outside or laterally of the support structure 108, but inside or medially of the outer housing part 103, in a way to allow inhaled and exhaled air to pass through the perforations or slots therein.

The outer housing part 103 and the inner housing part 102 are connectable along a contact plane at the proximal end of the outer housing part 103. The outer housing part 103 and the inner housing part 102 may thus be connectable along the periphery of the base plate 105. The outer housing part 103 is bulging distally from the neck of the wearer, during use. As such the outer housing part 103 will form or constitute a cage, enclosing the pinch plate 106, the flange 107, and the support structure 108. Suitable bulging shapes are dome shaped, elliptically dome shaped, cube shaped, cone shaped, etc., as long the outer surface of the outer housing part 103 extends distally from the contact plane with the inner housing part 102, allowing for an increase in inner surface in comparison with the cross sectional area of the outer housing part 103 along said contact plane, i.e. the cross sectional area of the base plate 105 in the transversal plane. In this way, the volume may be effectively used, whereby dead space is decreased, making the device smaller.

The outer housing part 103 has gripping means 109 distributed circumferentially of the proximal end of the outer housing part 103, for gripping the periphery of the inner housing part 102, such that the two are brought into connected cooperation. The gripping means 109 may be a gripping flange extending circumferentially of the outer housing part 103. The gripping flange may then be somewhat laterally displaced when pushed against the inner housing part 102, until it snaps over the outer edge of the base plate 105 on the inner housing part 102. The outer edge of the base plate 105 and or the gripping means 109 may have corresponding slanting surfaces for facilitating cooperation between the inner housing part 102 and the outer housing part 103. Also, the inner housing part 102 may be welded to the outer housing part 103.

The outer housing part 103 is perforated, or provided with ribs, extending distally to the top of the outer housing part 103, where the ribs connect at a connection point in the distal top of the outer housing part 103. Naturally, the space between the ribs may then form slots through which inhaled and exhaled air may pass during use of the breathing protector.

Figure 2:
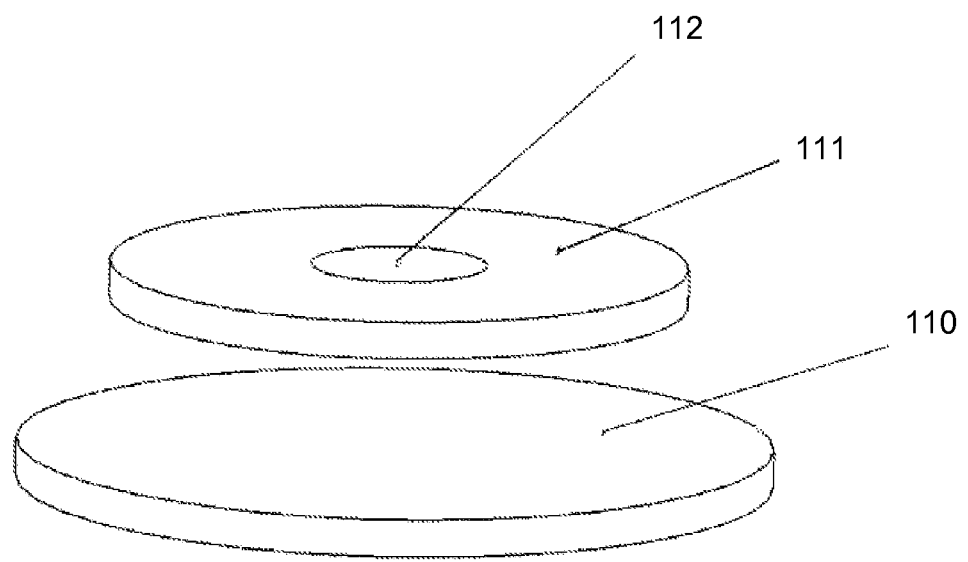
FIG. 2 is a perspective view if filter body and heat moisture exchanging body in a non-arranged state.

Along the inner surface of the outer housing part 103, a filter body 110 is arranged. In this way, the filter body 110 may be kept from coming into contact with contaminating items, such as fingers etc. Also, the volume of the breathing protector is used in a maximized way in respect of filtering area/effect. The filter body 110 may have a circular shape, with a preferred diameter of 50 to 70 mm. The filter body 110 may for example be an electrostatic filter, made of polypropylene. The filter body is pressed by the support structure 108 to conform to the inner surface of the outer housing part 103, whereby large interaction area with exhaled and inhaled air is kept. The filter body 110 is pinched between the pinch plate 106 and the outer housing part 103, such that its position may be maintained. Also, the pinching of the filter body between the outer housing part 103 and the pinch plate 106 decreases the risk of bacteria and virus entering the interior of the breathing protector. Also, this arrangement allows for the avoidance of additional filter body attachment means, such as glue. The filter body 110 is disclosed in FIG. 2 in non-arranged state.

Medially of the filter body 110 and laterally of the supporting structure 108, a heat moisture exchanging body 111 is arranged. The heat moisture exchanging body 110 may have the same diameter as the filter body 110, and thus also be pinched between the pinch plate 106 and the outer housing part 103. The heat moisture exchanging body 111 may also have a smaller outer diameter, such that the heat moisture exchanging body 111 ends at distally of the pinch plate 106. The, the heat moisture exchanging body 111 is not pinched together with the filer body 110, between the pinch plate 106 and the outer housing part 103. Then moisture accumulation at the pinch plate 106 may be decreased. The heat moisture exchanging body 111 may be manufactured in a suitable foam for such heat moisture exchanging bodies, as known in the art. The foam may also be impregnated with calcium chloride, to increase heat moisture exchanging ability. Centrally, the heat moisture exchanging body 111 may be provided with a through hole 112, such that the heat moisture exchanging body 111 is configured in a ring shape. In this way the height of the breathing protector may be reduced, while maintaining adequate functionality of the breathing protector with respect to heat moisture exchanging property. The heat moisture exchanging body 111 is disclosed in FIG. 2 in non-arranged state.

Of course, when other shapes than circular shape of the base plate 105 is used, naturally the filter body 110 and the heat moisture exchanging body 111 may be configured into corresponding shapes, instead of circular.

Figure 3:
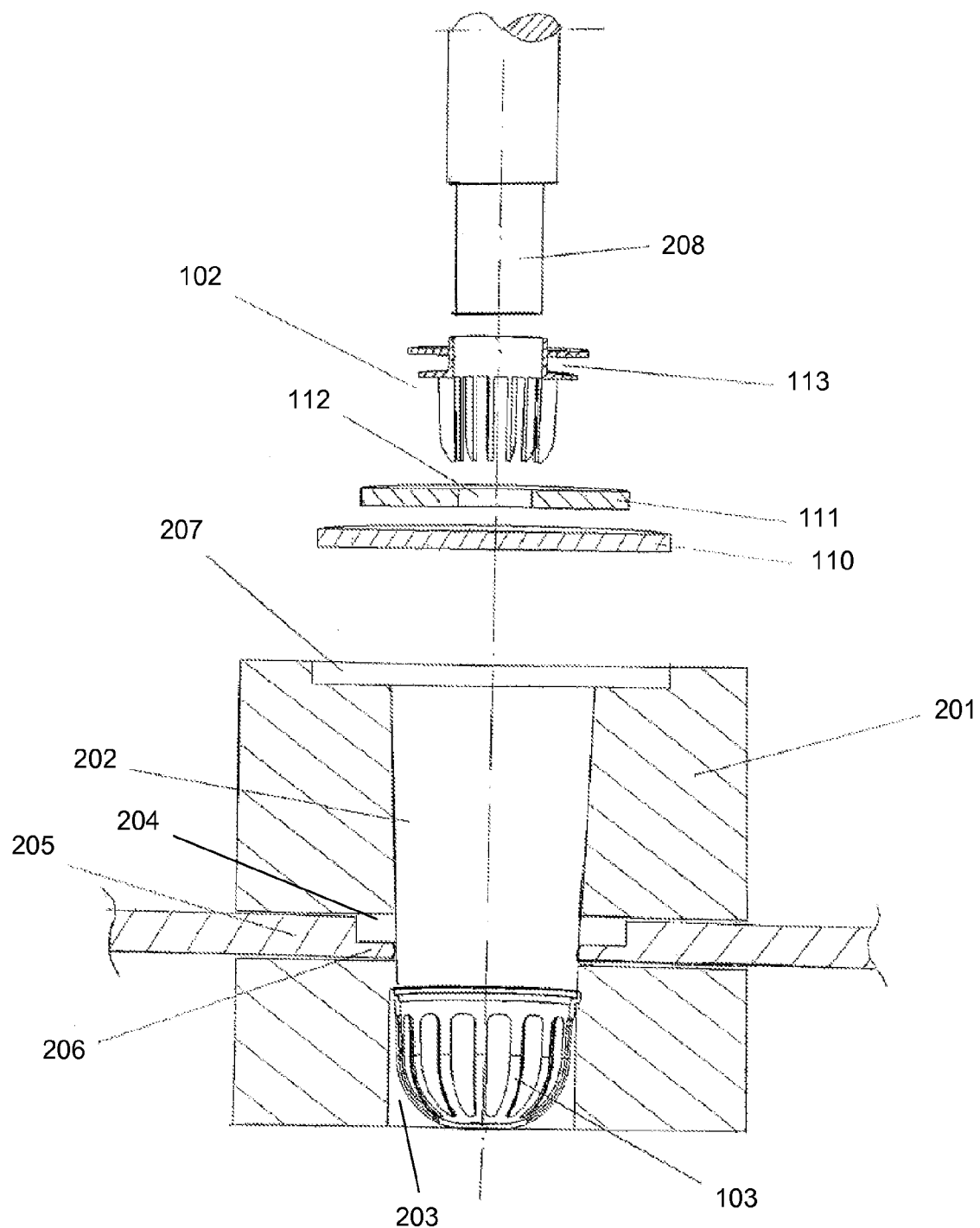
FIG. 3 is a cross sectional and exploded view of a breathing protector mounting assembly according to one embodiment of the present invention in a first position, together with components of a breathing protector.
Figure 4:
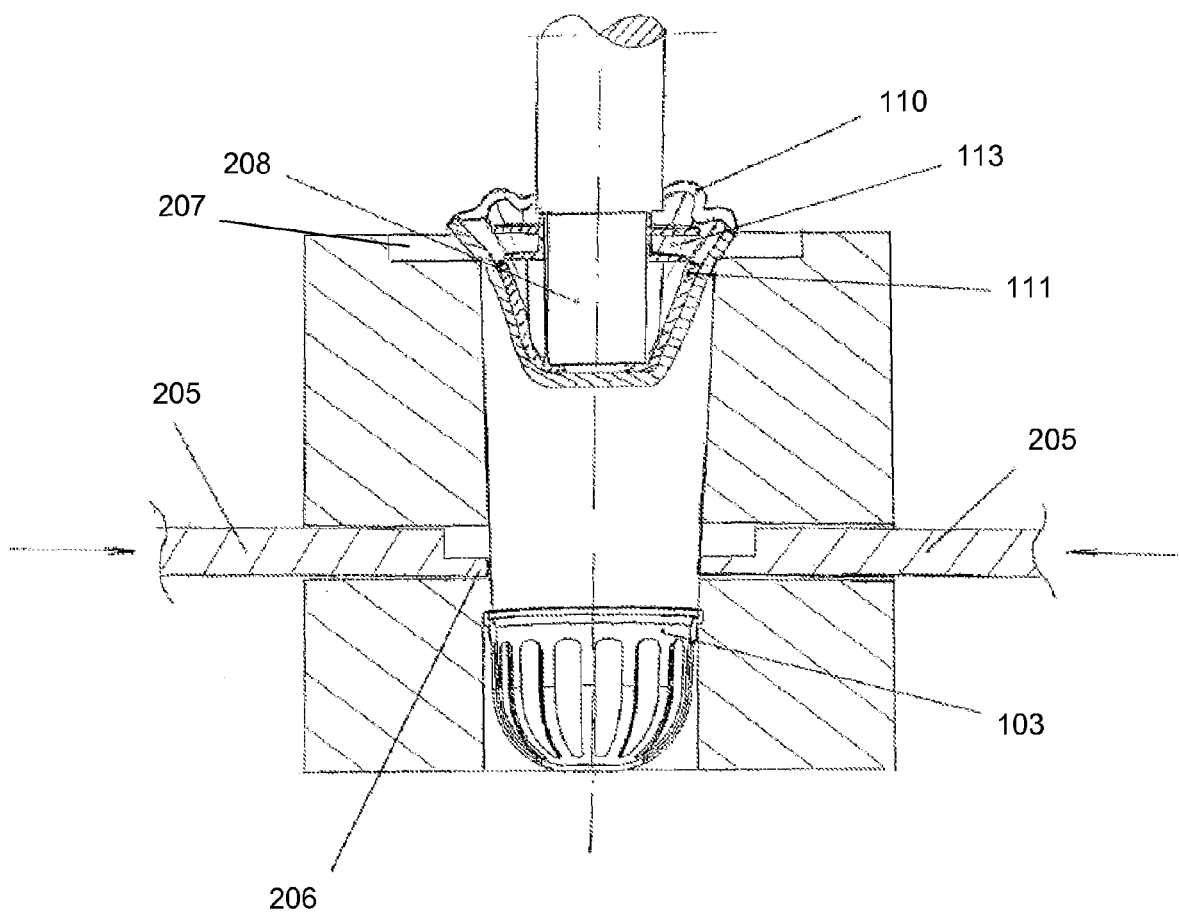
FIG. 4 is a cross sectional and exploded view of a breathing protector mounting assembly according to one embodiment of the present invention in a second position, together with components of a breathing protector.

In FIGS. 3 and 4 a breathing protector assembling tool and a method for assembling a breathing protector are disclosed. The breathing protector assembling tool comprises a fixture part 201 for holding the outer housing part 103 in an assembly position. The fixture part 201 comprises a cavity 202 for receiving the outer housing part 103. The cavity 202 may have a negative conical shape, i.e. that the cavity becomes narrower with depth, such that the outer housing part 103 may be inserted through the opening of the cavity, and displaced into the cavity until the outer housing part 103 get stuck in the cavity 202. In another embodiment, the cavity proceeds all through the fixture part 201, such that the outer housing part 103 may be inserted from beneath into an outer housing part seat 203. Transversally to the longitudinal extension of the cavity 202, channels 204 for receiving filter adjustment sticks 205 are arranged. The adjustment sticks 205 have adjustment pins 206. These adjustment pins correspond in width to the groove 113 between the base plate 105 and the pinch plate 106, such that the adjustment pins 206 can press the filter body 110 into the groove 113, once the inner housing part 102, covered by the heat exchanging body 111 and the filter body 110, has been advanced from the top into the cavity 202 into a position where the groove 113 is at the same height as the pins 206. The adjustment pins 206 may be semicircular towards the cavity 202, such that the pins enclose the inner housing part 102, and push the filter body 110 into the groove 113 along the circumference of the groove 113.

At the top surface of the fixture part 201, a filter body seat 207 may be arranged circumferentially of the cavity 202. The filter body 105 may then be arranged in said filter body seat 207, where after the heat moisture exchanging body 111 may be placed on top. Subsequently, the inner housing part 102 may be pressed onto the filter body 110 and the heat exchanging body 111 to press them all into the cavity into later cooperation with the outer housing part 103. The inner housing part 102 may be pressed into the cavity with aid of a pressing part 208. The pressing part 208 may preferably be a cylindrical rod, corresponding to—or having a somewhat smaller diameter than—the diameter of the cylindrical body 104 of the inner housing part 102. When the cavity 202 has a negative conical shape, i.e. that the cavity becomes narrower with depth, the filter body 110 and the heat exchanging body 111, together with the inner housing part 102, may be pressed downwards into the cavity 202 by the pressing part 208, such that the filer body 110 and the heat exchanging body 111 successively close in towards the inner housing part 102. In this way, the alignment of the different parts may be improved. Once the inner housing part 102 has traveled down into the cavity 202 to a position where the groove 113 and the channels 204, and thus the adjustment sticks 205 and adjustment pins 206, are substantially aligned, the adjustment sticks 205 are pushed inwardly/medially, such that the adjustment pins 206 presses the filter body 110 and optionally the heat moisture exchanging body 111 into the groove 113. Then the adjustment sticks 205 and the adjustment pins 206 are retracted, and the pressing part 208 is further pressed down into the cavity 202, until the inner housing part 102 is brought into cooperation with the outer housing part 103. The cooperation may be realized by pushing the inner housing part, such that the gripping means 109 snaps into cooperation with the base plate 105.

When the filter body 110 is pushed by the inner housing part 102 in the assembly tool, the filter body will assume a corrugated shape, thus allowing for an increase in surface area in small volume, resulting in decreased dead space. Simultaneously, the distal top part will remain flat, allowing for adequate height of the device. Hence the filter body 110 and/or the heat moisture exchanger 111 may be arranged in between the outer housing part 103 and the support structure 108 in a corrugated/pleated form, while the distal part, i.e. the top of the filter body 110 and/or the heat moisture exchanging body 111 is substantially flat, and extends transversally to the central axis A.

The embodiments according to the present invention allows for a breathing protector comprising a minimal number of components. Also, the components of the breathing protector disclosed herein may be manufactured in inexpensive manufacturing materials. The manufacturing process is easy to automate, whereby manufacturing costs are kept down.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A breathing protector, comprising:
   an inlet and an outlet, wherein an air flow is configured to pass from the inlet to the outlet into a trachea, a filter housing including an inner housing part, an outer housing part, and a filter body;
   wherein the inner housing part includes the outlet, a tracheal tube fitting and a support structure extending longitudinally and distally from the tracheal tube fitting toward a distal portion of the outer housing part, a base plate arranged in a proximal zone of the tracheal tube fitting and extending radially outwards from the tracheal tube fitting;
   wherein the outer housing part includes the inlet and forms a cage enclosing the support structure; and
   wherein the filter body is pressed by the support structure against the outer housing part, thereby conforming the filter body between the support structure and the outer housing part, further comprising a heat moisture exchanger arranged between the support structure and the outer housing part.

2. The breathing protector according to claim 1, wherein the inner housing part includes a pinch plate arranged distally of the base plate.

3. The breathing protector according to claim 2, wherein the pinch plate extends radially outwards from the tracheal tube fitting, wherein the filter body is pinched between the pinch plate and the outer housing part.

4. The breathing protector according to claim 2, wherein the base plate extends laterally beyond the pinch plate, and the outer housing part extends distally from the base plate.

5. The breathing protector according to claim 1, wherein the heat moisture exchanger is arranged between the support structure and the filter body.

6. The breathing protector according to claim 1, wherein the heat moisture exchanger is arranged distally of a pinch plate such that the heat moisture exchanger is not pinched to the filter body.

7. The breathing protector according to claim 1, wherein the heat moisture exchanger defines a through hole.

8. The breathing protector according to claim 1, wherein the tracheal tube fitting is a cylindrical body.

9. The breathing protector according to claim 8, wherein the cylindrical body has a central axis A and extends longitudinally in the proximodistal direction, and the cylindrical body has a slightly decreasing cross sectional area in the transversal plane when moving distally along the central axis A.

10. The breathing protector according to claim 1, wherein the support structure includes at least one of support fingers, support bars, and support ribs, each defining slots there between.

11. The breathing protector according to claim 1, wherein the inner housing part and the outer housing part are connected along a contact plane at a proximal end of the outer housing part.

12. The breathing protector according to claim 11, wherein the inner housing part and the outer housing part are connectable along a periphery of the base plate.

13. The breathing protector according to claim 11, wherein the outer housing part includes a gripping element distributed circumferentially of the proximal end of the outer housing part configured to grip a periphery of the inner housing part for bringing the outer housing part and inner housing part into connected cooperation.

14. The breathing protector according to claim 13, wherein the gripping element is a gripping flange extending circumferentially of the outer housing part.

15. The breathing protector according claim 1, wherein the inner housing part is welded to the outer housing part.

16. The breathing protector according to claim 1, wherein the outer housing part is at least one of perforated and provided with ribs, such perforation or ribs extending distally to a top of the outer housing part to a connection point.

17. The breathing protector according to claim 9, wherein the filter body is arranged in at least one of a corrugated and pleated form in at least a part between the inner housing part and the outer housing part.

18. The breathing protector according to claim 17, wherein a distal top part of the filter body is substantially flat, extending transversally to the central axis A of the breathing protector.

19. The breathing protector according to claim 5, wherein the heat moisture exchanger is arranged in at least one of a corrugated and pleated form in at least a part between the inner housing part and the outer housing part.

20. The breathing protector according to claim 2, wherein a groove is arranged between the base plate and the pinch plate on the inner housing part.

21. The breathing protector according to claim 1, wherein an outer surface of the support structure is complementary to the inner surface of the cage such that the filter body is conformed to the inner surface continuously.

22. The breathing protector according to claim 1, wherein the cage is dome shaped.

23. The breathing protector according to claim 1,
   wherein the cage bulges distally away from a contact plane with the base plate of the inner housing part such that an inner surface of the cage has a greater surface area than a cross sectional area of the base plate; and
   wherein the support structure is shaped to conform the filter body to the inner surface of the cage.

* * * * *